… … …

United States Patent

Heiser et al.

[11] Patent Number: 5,993,205
[45] Date of Patent: Nov. 30, 1999

[54] ORTHODONTIC BRACKET

[76] Inventors: Wolfgang Heiser, Dr.-Stumpf-Strasse 73, A-6020 Innsbruck, Austria; Claus Schendell, Gutenbergstrasse 9, D-82205 Gilching, Germany

[21] Appl. No.: 08/607,973

[22] Filed: Feb. 29, 1996

[51] Int. Cl.$^6$ .................................................. A61C 3/00
[52] U.S. Cl. ........................................ 433/8; 433/9
[58] Field of Search ................... 433/8, 9, 10, 16, 433/17

[56] References Cited

U.S. PATENT DOCUMENTS

| | | | |
|---|---|---|---|
| 3,345,745 | 10/1967 | Müller | 433/9 |
| 3,936,939 | 2/1976 | Faunce | 433/9 |
| 4,386,908 | 6/1983 | Kurz | 433/8 |
| 5,022,854 | 6/1991 | Broughton et al. | 433/8 |

OTHER PUBLICATIONS

American Orthodontics, Bulletin 3–78–1, 1714 Cambridge Ave, Sheboygan, Wisconsin 53081, 1978.

*Primary Examiner*—Ralph A. Lewis
*Attorney, Agent, or Firm*—Brooks Haidt Haffner & Delahunty

[57] ABSTRACT

An orthodontic bracket comprising a base plate having an edge configuration in which the mesial and distal edges are formed to extend in parallel to mesial and distal secants of the tooth crown. Those secants extend close to the mesial and distal edges of the tooth's crown when seen in front view between the mesial and distal junctions of the enamel, respectively, and the cement at the gingival edge of the tooth and the junction of the incisal edge or cusp and the mesial and distal edge, respectively, of the tooth's crown. Thereby, the positioning of the bracket in conformity with the anatomy of the tooth's crown is facilitated.

4 Claims, 4 Drawing Sheets

ORTHODONTIC BRACKET

The present invention relates to an orthodontic bracket having a base plate for mounting on a tooth and having sight lines utilised to facilitate alignment and positioning of the bracket on the tooth.

BACKGROUND OF THE INVENTION

There are numerous tooth configurations and sizes which vary from one patient to another. In most cases, however, the teeth of the majority of people conform to certain profiles and sizes, such that orthodontic brackets mounted on the teeth can also be standardised to correspond to certain tooth sizes and configuration.

With the advance of higher quality casting and finishing processes, the sizes of orthodontic brackets have gotten smaller, in particular to reduce the cost of raw materials and for aesthetic purposes so as to draw less attention to the patient. However, the smaller the brackets are the more experience the orthodontist needs for properly mounting the brackets to the teeth of a patient.

From U.S. Pat. No. 5,022,854 an orthodontic bracket is known which aims to obviate the problems in aligning and positioning the bracket on the tooth. This known bracket has a trapezoidal configuration comprising a pair of tie wings, each having non-parallel mesial and distal edges and further having an occlusal edge sustantially parallel to the occlusal plane of the tooth and to a sight line defined by the archwire slot formed through the tie wings. The edges of the tie winge form sight lines that intersect at a focal point located at the tip of the tooth root to assist in positioning the bracket. Further, a V groove is provided along the longitudinal axis of the bracket to form a sight line that also intersects the focal point. However, the location of this focal point can only be verified with the aid of X-rays so the orthodontist must compare the real tooth with its X-ray image when applying the bracket to the tooth. Further, it is to be noted that although this crowns of the teeth conform to certain profiles and sizes the tips of the teeth's roots sometimes deviate from the focal point defined by the intersection of the sight lines of the bracket. Bringing the focal point of the bracket into alignment with the tip of the tooth root then results in a misalignment of the bracket with respect to the visual surface of the tooth.

It is thus, an object of the present invention to provide an orthodontic bracket which enables an increase in the accuracy in aligning and positioning the bracket on the tooth. It is a further object of the invention to reduce the amount of time that a patient is in the chair while the orthodontist is mounting brackets. It is a still further object of the invention to provide an orthodontic bracket that will reduce the likelihood that an orthodontist will have to re-mount the bracket to correct for misalignmeat between the bracket and the tooth.

SUMMARY OF THE INVENTION

In accordance with the present invention, an orthodontic bracket is provided having a base plate for mounting on a tooth said base plate comprising non-parallel mesial and distal edges forming sight lines which intersect at a focal point at a location other than the tip of the tooth root, said sight lines for aligning and positioning the bracket in relation to mesial and distal edges of the tooth, an incisal edge forming a sight line for aligning and positioning the bracket in relation to the incisal edge of a central or lateral tooth, and to the occlusal plane of a tooth other than a central or lateral, respectively, wherein said mesial and distal edges of said base plate are adapted to extend substantially parallel to mesial and distal secants, respectively, of the tooth, said secants extending close to the mesial and distal edges of the tooth crown when seen in front view between the junction of the enamel and the cement at the gingival edge of the tooth crown on the one hand, and the junction of the mesial and distal edge, respectively, of the tooth's crown, and the incisal edge of a central or lateral tooth and the adjacent cusp of a tooth other than a central or lateral, respectively, on the other hand.

Thus, the other hand junctions by which the secants are defined, are differently defined depending on the type of tooth. The front teeth, i.e. the centrals and laterals, have almost linear incisal edges so that the location where a secant extends is clearly defined by the junction of the incisal edge and the rounded end portion of the adjacent mesial or distal edge of the crown. Cuspids and bicuspids, however, do not have an incisal edge but have one or more cusps, so that the location where a secant extends is defined by the junction of the cusp and the adjacent mesial or distal edge of the crown, respectively. In view of the fact that the teeth of the majority of people conform to certain profiles and sizes, as explained above, the location of said secants are in respective conformity so that the outlines of the base plates of the brackets may be standardised accordingly, as set forth by this invention.

In accordance with a preferred embodiment of the invention the gingival edge or the base plate is formed arcuately so as to extend parallel to the gingival edge of the tooth's crown.

The benefit of the invention resides in the fact that no longer the tooth's root but, rather, the anatomy of the tooth's crown is utilised for determining the exact position of the bracket when fixing it to the visible surface thereof. This improves the visual appearance, and the working speed of the orthodontist.

The base plate of the bracket is preferably a moulded element, e.g. from stainless steel or is milled from a suitable stainless steel raw material. Other materials like ceramic or plastics may be used as well.

DESCRIPTION OF THE PREFERRED EMBODIMENTS

Figure 1:
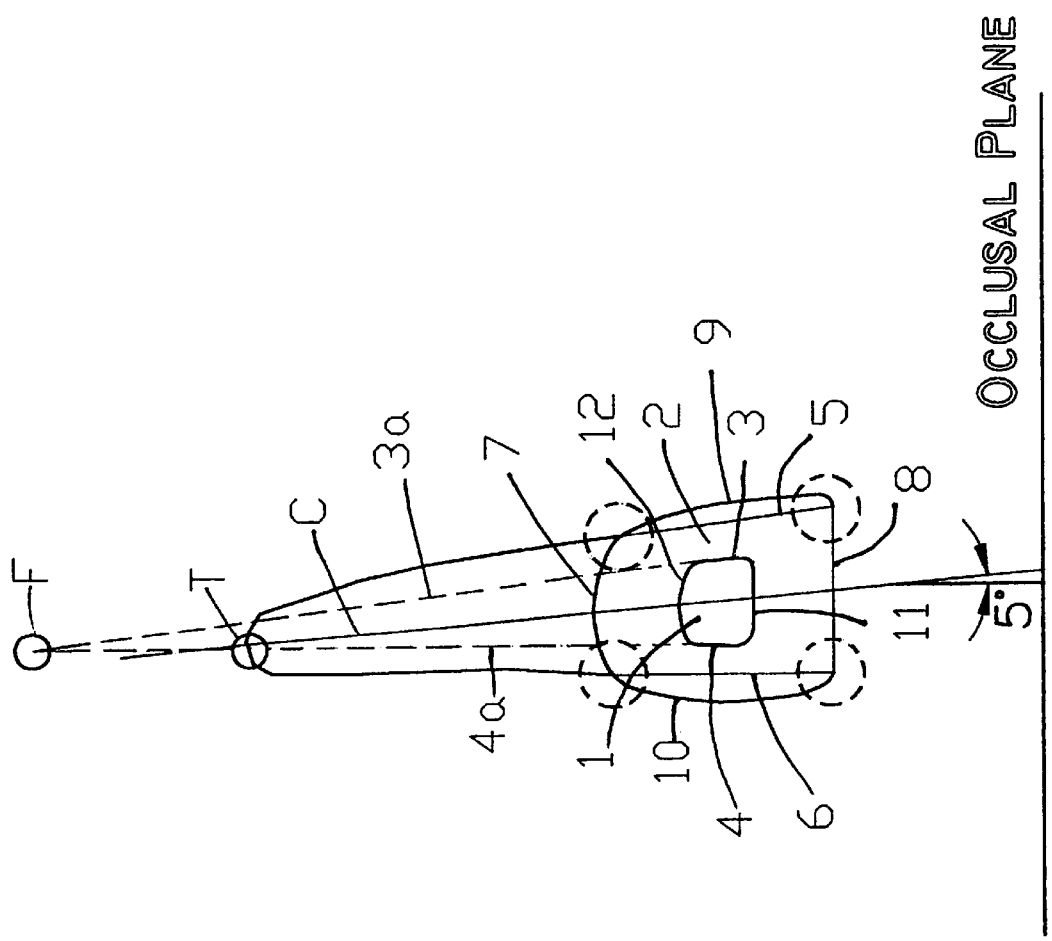
FIG. 1 is a front elevational view of an upper central tooth having a bracket mounted thereon of which just the outline of a base plate is shown.

FIG. 1 shows the outlines of a base plate 1 of a bracket mounted onto the front surface of an upper central #11. The tie wing (not shown) of the bracket may have any suitable shape, as e.g. shown in U.S. Pat. No. 5,074,783. A detailed explanation thereof may, thus, be omitted. The base plate is constructed to conform to the tooth surface 2 upon which the base plate 1 of the bracket is removably attached by known means. The configuration of the base plate is such that it imparts torque into the tie wing (not shown) integrally formed therewith. In this instance, integral is defined to mean all one part, i.e. the base plate and the tie wing forming the bracket would be a cast or milled part not requiring any assembly.

The base plate has a mesial edge 3 and a distal edge 4 defining sight lines 3a and 4a which intersect at a focal point F which is different from the tip T of the tooth to the front surface 2 of which the bracket is mounted. The mesial and distal edges 3 and 4 of the base plate 1 extend parallel to secants 5 and 6 of the tooth defined by its anatomy.

The mesial secant 5 extends between the mesial junction of the enamel of the tooth's crown when seen in front view as in FIG. 1 and the cement at the gingival edge 7 of the crown on the one hand, and the junction of incisal edge 8 and the mesial edge 9 of the crown, i.e. where the rounded corner of the mesial edge 9 joins the incisal edge 8 on the other hand. Similarly, the distal secant 6 extends between the distal junction of the enamel arid the cement at the gingival edge 7 at the distal side of the tooth and the respective junction of the incisal edge 8 and the distal edge 10 of the tooth's crown, i.e. where the rounded corner thereof merges into the incisal edge 8.

Further, the base plate 1 of the bracket comprises an incisal edge 11, which is parallel to the incisal edge 8 of the crown .

Preferably, the gingival edge 12 of the base plate 1 is rounded so as to extend parallel to the gingival edge 7 of the crown.

As may be seen from FIG. 1, the centre line C of the tooth which extends through the tip T of the root is inclined with respect to the incisal edge 8 which is situated in the occlusal plane of the set of teeth. This inclination, also called angulation, is usually 5 degrees for the upper centrals, as shown in FIG. 1. The angulation is different for the different teeth of a set of teeth, as shown in FIG. 3.

Figure 2:
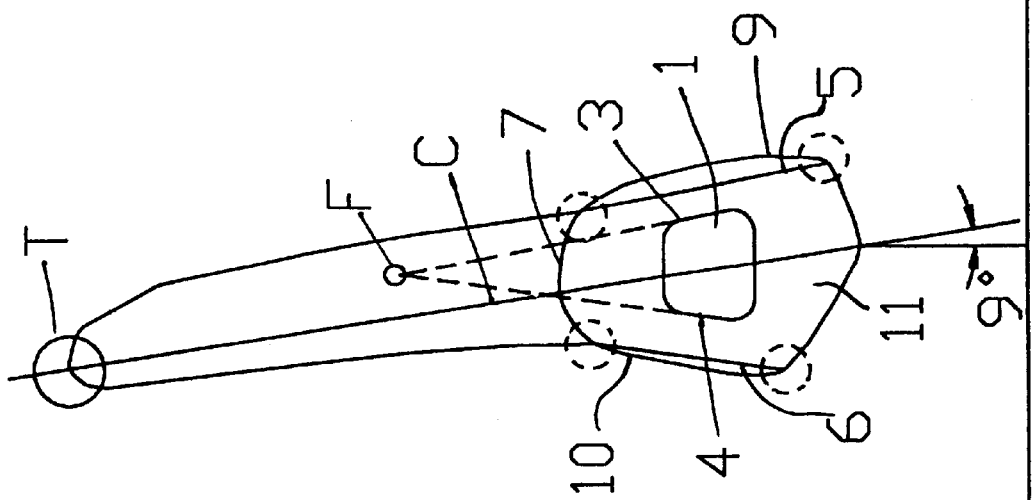
FIG. 2 is a view similar to that of FIG. 1 of a cuspid having a bracket mounted thereon.

FIG. 2 is a representation similar to that of FIG. 1, but applied to an upper cuspid #13. As is known, a cuspid does not have an incisal edge, but comprises cusp so that it is not possible end points of the secants by means of an incisal edge. Rather, as may be seen from FIG. 2, the mesial secant 5 extends between the incisal junction of the enamel of the tooth's crown when seen in front view and the cement at the gingival edge 7 of the crown on the one hand, and the junction of the cusp 13 and the mesial edge 9 of the crown on the other hand. In a similar manner, the distal secant 6 extends between the distal junction of the enamel of the tooth's crown when seen in front view and the cement at the gingival edge 7 of the crown on the one hand, and the junction of the cusp 13 and the distal edge 10 of the crown on the other hand. In accordance with the invention, the mesial and distal edges 3 and 4 extend in parallel to the mesial and distal secants 5 and 6, respectively. Further, as may clearly be seen from FIG. 2, the focal point F of the mesial and distal edges of the base plate 1 is at a location different from that of the tip T of the tooth root.

Figure 3:
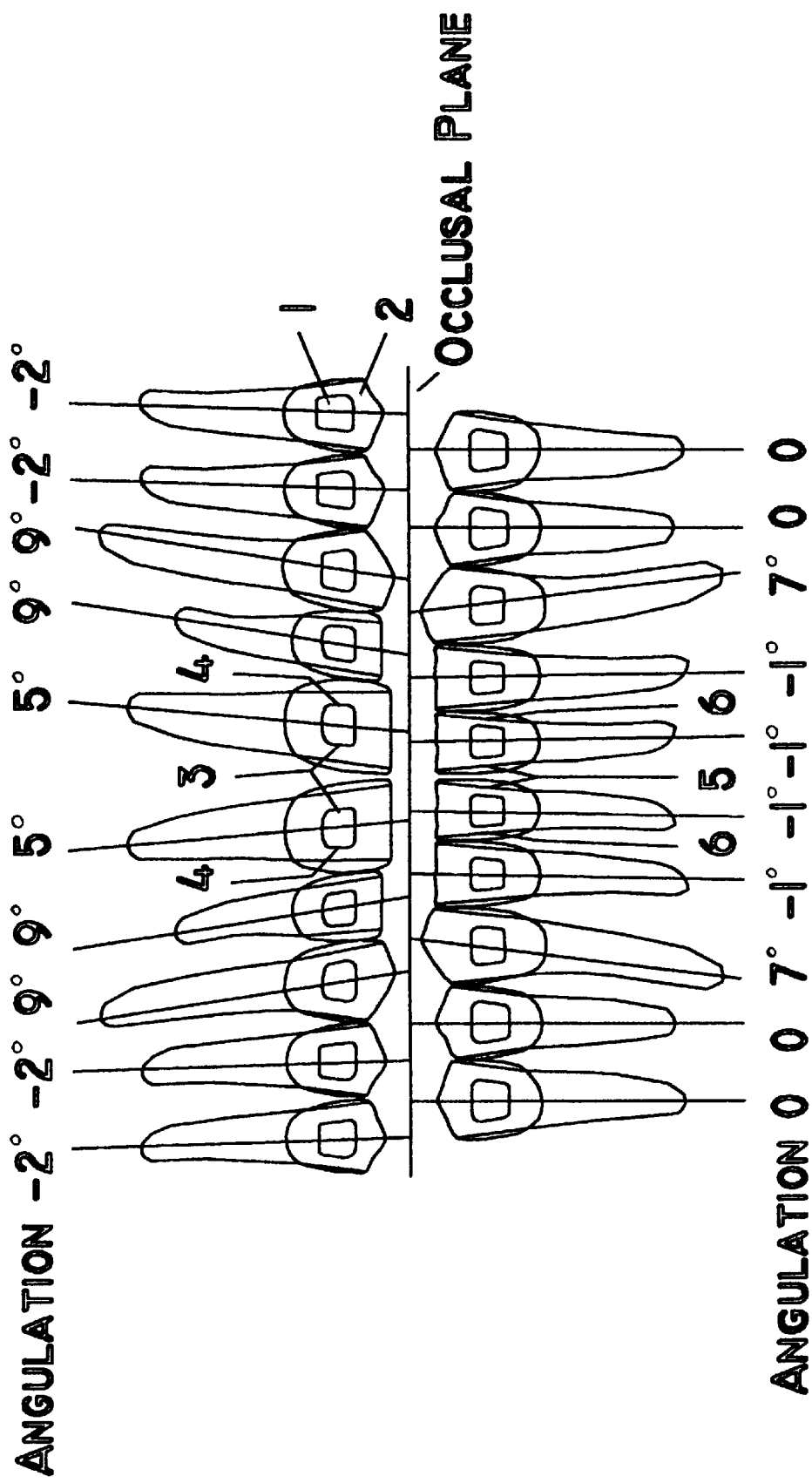
FIG. 3 is a set to ten teeth having brackets mounted thereto, only the outline of the base plates thereof being shown.

FIG. 3 shows a set of ten upper and lower teeth in correct alignment showing the outline of the base plates of brackets at the end of an orthodontic treatment. As may be seen from FIG. 3, the base plates have different shapes dependent on the type of tooth. In the drawings, the secants of each of the teeth are shown, and it is to be noted that the mesial and distal edges of the base plates are always parallel to the respective secants.

It may be seen from FIG. 3 that the gingival edge of the upper centrals and upper laterals are rounded so as to conform with the gingival edges of the teeth crowns whereas the gingival edges of the brackets associated to the other teeth are linear as those teeth are not so dominant. It may further be seen from FIG. 3 that the angulations of the upper centrals are 5 degrees, of the upper laterals and upper cuspids are 9 degrees and of the upper bicuspids #14, 15 and #24, 25 are −2 degrees whereas the angulations of the lower centrals and lower laterals are −1 degrees each, of the cuspids are 7 degrees and the lower bicuspids #34, 35 and #44, 45 are 0 degrees each.

Figure 4:
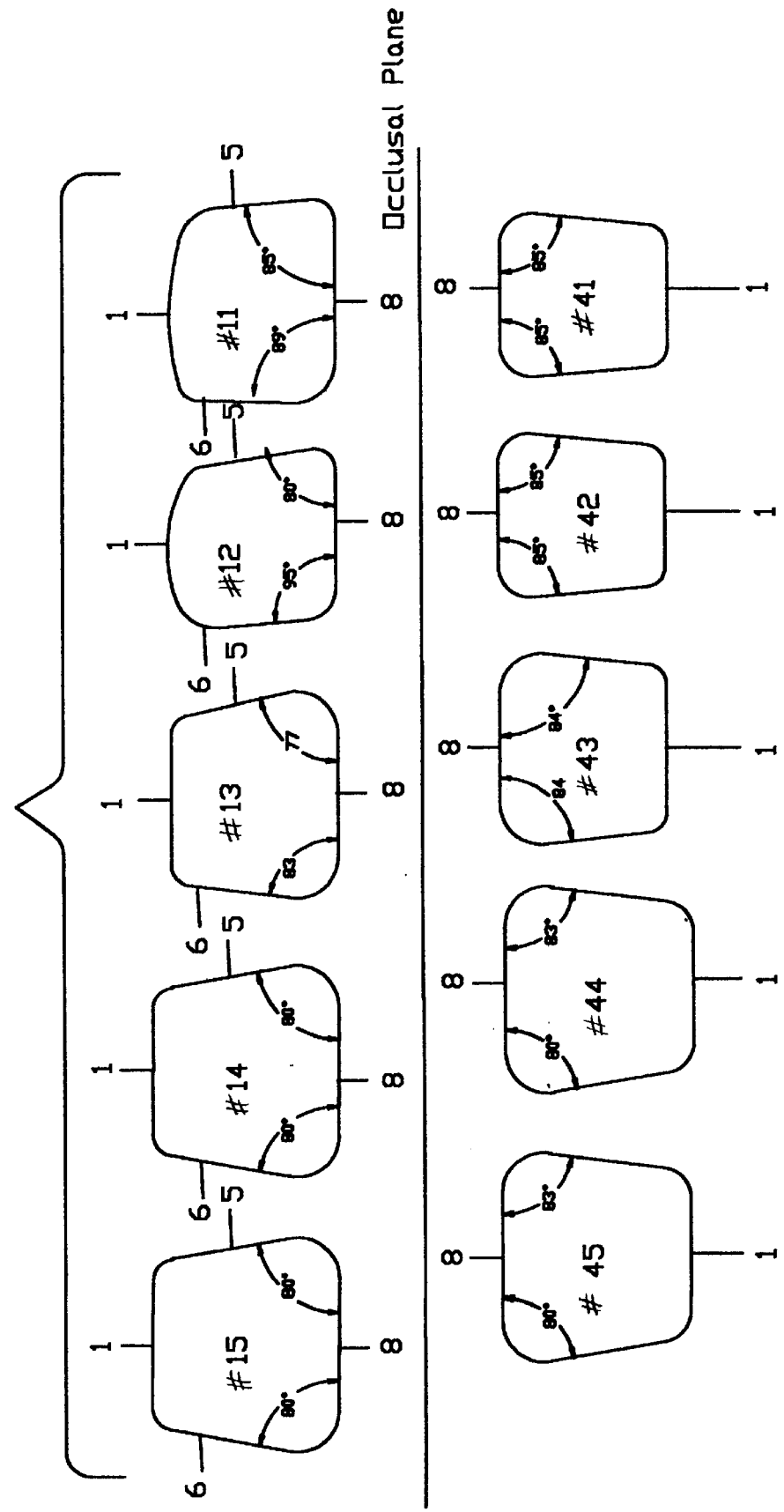
FIG. 4 is a top elevational view of a set of base plates to be used at the right side of a set of teeth.

FIG. 4 shows top elevational views of the base plates of the teeth #11–15 and #41–45 of one side of the set of teeth shown in FIG. 3. From FIG. 4 the angles of the mesial and distal edges with respect to the occlusal plane which in parallel to the occlusal edges 8 of the base plates may be taken as follows:

| TOOTH | MESIAL EDGE | DISTAL EDGE |
|---|---|---|
| #11 | 85° | 89° |
| #12 | 80° | 95° |
| #13 | 77° | 83° |
| #14 | 80° | 80° |
| #15 | 80° | 80° |
| #41 | 85° | 85° |
| #42 | 85° | 85° |
| #43 | 84° | 84° |
| #44 | 83° | 80° |
| #45 | 83° | 80° |

Brackets having these outlines satisfy applications with most of the patients in practice. it should be noted that the aforementioned angles may vary by a few degrees without leaving the scope of this invention.

It is to be understood that FIG. 4 shows the base plates for a fixture to the right half of the set of teeth and that a similar set of base plates having shapes symmetrical to those shown in FIG. 4 are for use with the left half of the set of teeth.

I claim:

1. A set of orthodontic brackets comprising first through fifth pairs of upper brackets having base plates to be removably attached respectively to the central incisors, the lateral incisors, the cuspids and the first and second bicuspids of the upper jaw of a patient, and first through fifth pairs of lower brackets having base plates to be removably attached respectively to the central incisors, the lateral incisors, the cuspids and the first and second bicuspids of the lower jaw of the patient, the base plates each having an occlusal edge, a mesial edge forming a first angle within the base plate with said occlusal edge, and a distal edge forming a second angle within the base plate with said occlusal edge, wherein said first and second angles of the first pair of upper brackets are 85° and 89°, respectively, said first and second angles of the second pair of upper brackets are 80° and 95°, respectively, said first and second angles of the third pair of upper brackets are 77° and 83°, respectively, said first and second angles of the fourth pair of upper brackets are 80° and 80°, respectively, said first and second angles of the fifth pair of upper brackets are 80° and 80°, respectively, said first and second angles of the first pair of lower brackets are 85° and 85°, respectively, said first and second angles of the second pair of lower brackets are 85° and 85°, respectively, said first and second angles of the third pair of lower brackets are 84° and 84°, respectively, said first and second angles of the fourth pair of lower brackets are 83° and 80°, respectively, and said first and second angles of the fifth pair of lower brackets are 83° and 80°, respectively.

2. The orthodontic bracket as set forth in claim 1, wherein the gingival edge of the base plate is arcuately formed so as to extend parallel to the gingival edge of the tooth's crown.

3. A method of positioning an orthodontic bracket according to claim 1 having a base plate for mounting the bracket and base plate on a tooth having a root comprising a tip, so that said base plate comprises non-parallel mesial and distal edges forming sight lines which intersect at a focal point at a location other than the tip of the tooth's root, using said sight lines for aligning and positioning the bracket in relation to mesial and distal edges of the tooth, an incisal edge forming a sight line for aligning and positioning the bracket in relation to the incisal edge of a central tooth or lateral tooth, or to the occlusal plane of a tooth other than a central tooth or lateral tooth, whereby said mesial and distal edges of said base plate extend substantially parallel to mesial and distal secants, respectively, of the tooth, said secants each extending close to the mesial and distal edges of the tooth's crown when seen in front view between the mesial and distal junctions of the enamel, respectively, and the cement at the gingival edge of the tooth's crown of the central or lateral tooth, and the junction of the mesial and distal edge, respectively, of the tooth's crown and the incisal edge of the central or lateral tooth, and the adjacent cusp of the tooth other than a central or lateral, respectively.

4. The method as set forth in claim 3, wherein the gingival edge of the base plate is arcuately formed so as to extend parallel to the gingival edge of the tooth's crown.

\* \* \* \* \*